(12) United States Patent
Ng et al.

(10) Patent No.: US 8,026,379 B2
(45) Date of Patent: Sep. 27, 2011

(54) PARICALCITOL INTERMEDIATES

(75) Inventors: Chze-Siong Ng, Taoyuan (TW); Ching-Peng Wei, Taoyuan (TW)

(73) Assignee: Formosa Laboratories, Inc., Taoyuan (TW)

(*) Notice: Subject to any disclaimer, the term of this patent is extended or adjusted under 35 U.S.C. 154(b) by 589 days.

(21) Appl. No.: 12/143,117

(22) Filed: Jun. 20, 2008

(65) Prior Publication Data
US 2009/0318722 A1    Dec. 24, 2009

(51) Int. Cl.
*C07J 9/00*    (2006.01)
(52) U.S. Cl. ..................................................... 552/653
(58) Field of Classification Search ................... 552/653
See application file for complete search history.

(56) References Cited

U.S. PATENT DOCUMENTS

| 5,342,975 | A | * | 8/1994 | DeLuca et al. | 552/653 |
| 5,354,744 | A | * | 10/1994 | DeLuca et al. | 514/167 |
| 5,710,294 | A | * | 1/1998 | DeLuca et al. | 552/653 |
| 6,359,012 | B1 | | 3/2002 | Meckler et al. | |
| 7,491,712 | B1 | * | 2/2009 | Ng et al. | 514/167 |
| 7,645,911 | B2 | * | 1/2010 | Ng et al. | 568/819 |
| 2007/0088007 | A1 | * | 4/2007 | Ng et al. | 514/167 |
| 2009/0149678 | A1 | * | 6/2009 | Ng et al. | 568/819 |

FOREIGN PATENT DOCUMENTS

DE    10 2008 061 497.1    12/2009

OTHER PUBLICATIONS

Office Action for corresponding German application 10 2008 061 497.1-43 which cites German application 10 2008 061 497.1-43.

* cited by examiner

*Primary Examiner* — Brandon Fetterolf
*Assistant Examiner* — Anna Pagonakis
(74) *Attorney, Agent, or Firm* — WPAT, P.C.; Anthony King (57) ABSTRACT

The present invention relates to a compound and a novel process for the preparation of Paricalcitol intermediates.

4 Claims, 3 Drawing Sheets

PARICALCITOL INTERMEDIATES

FIELD OF THE INVENTION

This invention relates to a compound and a process for preparation of Paricalcitol intermediates

BACKGROUND OF THE INVENTION

It is well known that the D vitamins exhibit certain biological effects, such as stimulation of intestinal calcium absorption, stimulation of bone mineral resorption and the prevention of rickets. It is also well known that such biological activity is dependent upon these vitamins being altered in vivo, i.e. metabolized, hydroxylated derivatives. For example, current evidence indicates that 1α,25-dihydroxyvitamin $D_3$ is the in vivo active form of vitamin $D_3$ and is the compound responsible for the aforementioned biological effects.

The synthetic 1α-hydroxyvitamin D analogs, such as 1α-hydroxyvitamin $D_3$, and 1α-hydroxyvitamin $D_2$ also exhibit pronounced biological potency and such compounds as well as the natural metabolites show great promise as agents for the treatment of a variety of calcium metabolism and bone disorders, such as osteodystrophy, osteomalacia and osteoporosis.

Since 1α-hydroxylation is an essential element in imparting biological activity to the vitamin D compounds and their derivatives there has been increasing interest in methods for chemically accomplishing such hydroxylation. Except for one suggested method for the total synthesis of 1α-hydroxyvitamin $D_3$, all syntheses of 1α-hydroxylated vitamin D compounds involved the preparation of a 1α-hydroxylated steroid, from which, after conversion to the corresponding 1α-hydroxy-5,7-diene sterol derivative, the desired vitamin D compound is obtained by well known photochemical methods.

Paricalcitol is a vitamin $D_2$ derived sterol lacking the carbon-19 methylene group found in all natural vitamin D metabolites. A novel class of vitamin D-related compounds, namely the 1α-hydroxy-19-nor-vitamin D analogs, as well as a general method for their chemical synthesis are disclosed in U.S. Pat. Nos. 5,710,294 and 5,342,975. Furthermore, U.S. Pat. No. 6,359,012 provides the method for making 24(s)-hydroxyvitamin $D_2$, which is the first stereospecific synthesis of 24(s)-hydroxyvitamin $D_2$ by coupling of (s)-(+)-2,3-dimethyl-2-triethylsilyloxybutyraldehyde and a vitamin D phosphine oxide derivative to form a C-3 and C-24 diprotected trans-vitamin $D_2$ which is then deprotected and irradiated to yield the 24(S)-hydroxyvitamin $D_2$.

SUMMARY OF THE INVENTION

The present invention provides a compound having formula I wherein $X_1$ is OH, O-acyl, O—$C_{1-8}$ alkylsilyl or O—$C_{1-8}$ alkyloxy-$C_{1-8}$ alkyl; $X_2$ is $C_{1-6}$ alkoxy; and $X_3$ is chlorine, bromine, iodine, O-tosyl or O-mesyl.

The present invention also provides a process for preparation of Paricalcitol intermediate having a formula 21

DETAILED DESCRIPTION OF THE INVENTION

Figure 1:
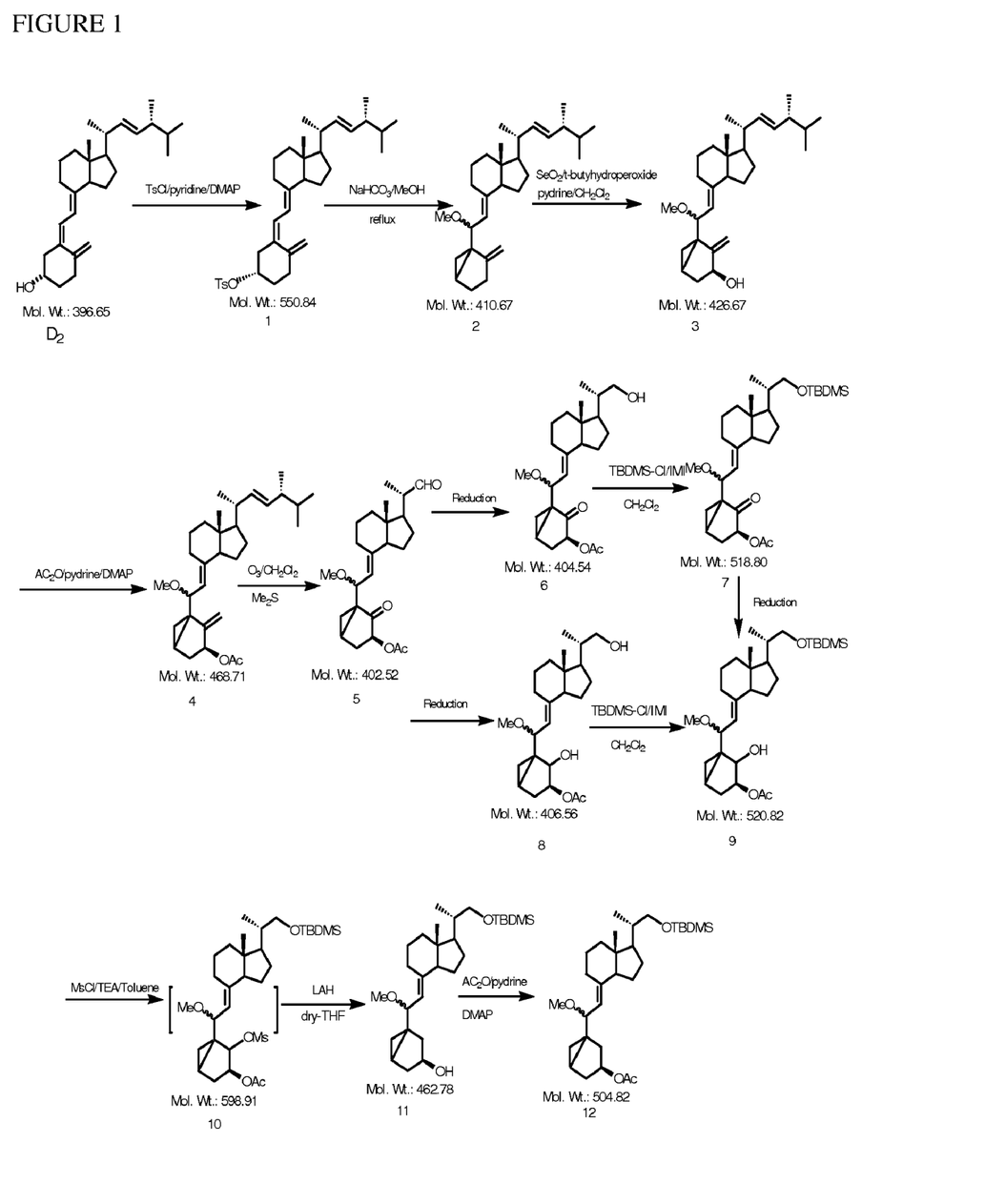
FIG. 1 is synthetic scheme for Paricalcitol intermediate.

The present invention provides a compound having formula I wherein $X_1$ is OH, O-acyl, O—$C_{1-8}$ alkylsilyl or O—$C_{1-8}$ alkyloxy-$C_{1-8\ alkyl}$; $X_2$ is $C_{1-6}$ alkoxy; and $X_3$ is chlorine, bromine, iodine, O-tosyl or O-mesyl.

In a preferred compound of the present invention, $X_2$ is methoxy. In other preferred compounds of the present invention, $X_1$ is hydroxyl, O-acyl or O-tert-butyldimethylsilyl. In more preferred compounds of the present invention, $X_3$ is iodine, O-tosyl or O-mesyl.

When describing the processes of this invention, the following terms have the following meanings unless otherwise indicated.

The term "alkyl" means a monovalent saturated hydrocarbon group which may be linear or branched. Unless otherwise defined, such alkyl group typically contain from 1 to 6 carbon atoms. Representative alkyl groups include, by way of example, methyl, ethyl, n-propyl, isopropyl, n-butyl, sec-butyl, isobutyl, tert-butyl, n-pentyl, n-hexyl, and the like.

The term "alkoxy" means a monovalent group of the formula (alkyl)-O—, where alkyl is as defined herein. Representative alkoxy groups include, by way of example, methoxy, ethoxy, n-propoxy, isopropoxy, n-butoxy, sec-butoxy, isobutoxy, tert-butoxy and the like.

The present invention provides a process for preparation of Paricalcitol intermediate having a formula 21 said process comprising converting the compound of formula 20 with TBDMS-chloride in the presence of an amine in an organic solvent.

In a preferred process of the present invention, the amine is imidazole and the organic solvent is $CH_2Cl_2$.

In the process of the present invention, the compound of formula 20 is obtained by converting the compound of formula 19 with a base in an organic solvent.

In a preferred process of the present invention, the base is NaOH and the organic solvent is methanol;

In the process of the present invention, the compound of formula 19 is obtained by reacting acetic acid with the compound of formula 18 at 30~60° C.

In the process of the present invention, the compound of formula 18 is prepared by converting a compound of formula 17 with diphenylphosphine and n-butyllithium in an organic solvent, followed by the treatment with an oxidizing agent.

In a preferred process of the present invention, the organic solvent is tetrahydrofuran, and the oxidizing agent is $H_2O_2$.

In the process of the present invention, the compound of formula 17 is prepared by converting a compound of formula 16 with sodium iodide in the organic solvent.

In the process of the present invention, the compound of formula 16 is obtained by converting the compound of formula 15 with TBDMS-chloride in the presence of an amine in an organic solvent.

In a preferred process of the present invention, the amine is imidazole and the organic solvent is CH$_2$Cl$_2$.

In the process of the present invention, the compound of formula 15 is prepared by converting the compound of formula 14 with a base in an organic solvent.

In a preferred process of the present invention, the base is NaOH, and the organic solvent is methanol.

In the process of the present invention, the compound of formula 14 is obtained by converting the compound of formula 13 with TsCl in the presence of CH$_2$Cl$_2$; pyridine and DMAP.

In the process of the present invention, the compound of formula 13 is obtained by reacting the compound of formula 12 with tertabutyammonium fluoride (TBAF) in THF.

In the process of the present invention, the compound of formula 12 is prepared by converting the compound of formula 11 with acetic anhydride (Ac$_2$O) in the presence of dry pyridine.

In the process of the present invention, the compound of formula 11 is obtained by reacting the compound of formula 10 with LiAlH$_4$ in dry THF.

In the process of the present invention, the compound of formula 10 is prepared by converting the compound of formula 9 with sulfonyl chloride in an organic solvent and an amine.

In a preferred process of the present invention, the organic solvent is toluene; the amine is triethylamine; and sulfonyl chloride is MsCl.

In the process of the present invention, the compound of formula 9 is obtained by converting the compound of formula 8 with TBDMS-chloride in the presence of an amine in an organic solvent.

In a preferred process of the present invention, the amine is imidazole and the organic solvent is CH$_2$Cl$_2$.

In the process of the present invention, the compound of formula 9 is also obtained by converting the compound of formula 7 via hydride reduction In the process of the present invention, the compound of formula 8 is prepared by converting the compound of formula 5 via reduction In the process of the present invention, the compound of formula 7 is prepared by converting the compound of formula 6 with TBDMS-chloride in the presence of imidazole in CH$_2$Cl$_2$.

In the process of the present invention, the compound of formula 6 is obtained by converting the compound of formula 5 via reduction

5

In the process of the present invention, the compound of formula 5 is prepared by reacting the compound of formula 4

4 with O₃ in CH₂Cl₂, followed by quenching with Me₂S.

In the process of the present invention, the compound of formula 4 is prepared by converting the compound of formula 3

3 with acetic anhydride (Ac₂O) in the presence of pyridine.

In the process of the present invention, the compound of formula 3 is prepared by converting the compound of formula 2

2 with $SeO_2$ and t-butylhydroperoxide in the presence of pyridine in $CH_2Cl_2$.

EXAMPLE

The examples below are non-limited and are merely representative of various aspects and features of the present invention.

Example 1

Preparation of 1-acetoxy-Cyclovitamin D₂ (4)

Into a 12 L G/L, three-neck, round-bottom flask equipped with a mechanical stirrer, was charged vitamin D₂ (500 g, 1.26 mol), dichloromethane (750 mL), pyridine (750 mL), 4-dimethylaminopyridine (DMAP, 30.8 g, 0.25 mol) and p-toluene-sulfonyl chloride (420.5 g, 2.20 mol) under nitrogen.

The mixture was allowed to react for 24 hr at below 10° C., and was then quench with 1500 mL of 10% $NaHCO_{3(aq)}$. The aqueous phase was extracted with ethyl acetate (2000 mL×2) and the ether acetate extract was washed with 10% $NaHCO_3$ (2000 mL×2), and $H_2O$ (2000 mL×2). The solvent was removed in vacuo and the crude residue (690 g, Vitamin D₂ 3-tosylate) that was used without purification in the next step.

To a 12 L, three-neck, round-bottom flask equipped with a reflux condenser, mechanical stirrer, thermocouple was charged with Vitamin D₂ 3-tosylate (690 g, 1.25 mol), sodium bicarbonate (1000 g, 12 mol), and methanol (7500 mL). The resulting suspension was heated under reflux for 2.5 hour or until TLC analysis (silica gel plates, 30% ethyl acetate in hexanes) indicated that no starting material remained. The reaction mixture was cooled to room temperature and filtered, and the filtrate was concentrated under reduced pressure. The crude residue was dissolved in ethyl acetate (2000 mL) and washed with $H_2O$ (2000 mL×2). The extracts was dried over anhydrous magnesium sulfate and filtered. The filtrate was evaporated under reduced pressure to obtain 514 g of compound 2 as yellow foam that was used without purification in the next step.

In 12 L, three-neck, round-bottom flask equipped with a mechanical stirrer, thermocouple, nitrogen bubbler was charged with compound 2 (514 g, 1.25 mol), $SeO_2$(84.1 g, 0.75 mol), $CH_2Cl_2$ (4500 mL) and pyridine (101 mL). The mixture was cooled below 15° C., and then tert-butyl hydroperoxide (70% t-BuOOH in water, 624.8 mL) was added. The mixture was allowed to react for 5 hr, and was then quench with 3000 mL of 10% $NaHCO_{3(aq)}$. The aqueous phase was extracted with ethyl acetate (2000 mL×2) and the ether acetate extract was washed with 10% $NaHCO_3$ (2000 mL×2), and $H_2O$ (2000 mL×2). The solvent was removed in vacuo and the crude residue {1-hydroxyl-Cyclovitamin $D_2$}. Silica gel column chromatography (20% ethyl acetate in hexanes as eluant) provided 275 g (0.64 mol) of compound 3 as yellow oil.

Compound 3 (275 g, 0.64.mol) was dissolved in pyridine (1376 mL) and acetic anhydride (197 g, 1.9 mol). The reaction was added 4-Dimethylaminopyridine (DMAP, 15.8 g, 0.13 mol) and kept at room temperature for about 1 hour, then diluted with 10% $NaHCO_3$ solution (1000 mL). This solution is extracted with ethyl acetate (2000 mL×3) and the organic extracts were washed with $H_2O$ (2000 mL×3), dried over $MgSO_4$, and the solvent was removed in vacuo to give crude compound 4 (302 g) that was used without purification in the next step.

Example 2

Preparation of
(20S)-aldehyde-10-oxo-1-acetoxy-Cyclovitamin (5)

Compound 4 (g, 0.64 mol) was dissolved in methylene chloride (300 mL) and methanol (30 mL), 10% $NaHCO_3$ (30 mL) were added. The mixture is cooled to −10° C. Ozone (generated from Oxygen, using Ozoner generator) was bubbled through the solution for 2 hour until TLC analysis (silica gel plates, 20% ethyl acetate in hexanes) indicated no further change.

The reaction mixture was purged with oxygen for 5 minutes, and sodium borohydride (6 g, 88.23 mmol) was added in five portions over 1 hours. The resulting mixture was stirred for 1 hour at room temperature. At this point, 0.5N aqueous hydrochloric acid solution (100 mL) was slowly added, and the mixture was extracted with 50% ethyl acetate in hexanes (200 mL×3). The combined organic extracts were washed with 10% $NaHCO_3$ (200 mL×3), dried over anhydrous magnesium sulfate, and filtered. The filtrate was evaporated under reduced pressure to obtain 86 g of 5 as orange foam. Silica gel column chromatography (10% ethyl acetate in hexanes as eluant) provided 5.2 g (30% yield) of compound 5 as yellow oil.

$^1$HNMR($CDCl_3$, 600 Hz):δ9.57(s, 1H), 5.13~5.16(m,1H), 4.58~4.70(m, 1H), 4.07~4.10(m, 1H), 3.18(s, 3H), 2.75~2.77(m,1H), 2.28~2.33(m, 1H), 2.09(s,3H), 2.00~1.21 (m,14H), 1.14(d,J=4.86 Hz, 3H), 0.56(d,J=5.46 Hz, 3H).

Example 3

Preparation of 1α-acetoxy-3,5-cyclo-(20S)-(tert-Butylmethylsilyloxy)-10-hydroxyl-19-nor vitamin D2 1-acetate, 6-methyl ether 1-acetate (9)

(a). Preparation of 1α-acetoxy-3,5-cyclo-(20S)-hydroxylmethyl-10-oxo-19-nor vitamin D2 1-acetate, 6-methyl ether 1-acetate (6)

Compound 4 (302 g, 0.64 mol) was dissolved in methylene chloride (2.2 Kg) and methanol (132 g), 10% $NaHCO_3$ (165 mL) were added. The mixture is cooled to −10° C. Ozone (generated from Oxygen, using Ozoner generator) was bubbled through the solution for 2 hour until TLC analysis (silica gel plates, 30% ethyl acetate in hexanes) indicated no further change.

The reaction mixture was purged with oxygen for 5 minutes, and sodium borohydride (30.5 g, 0.81 mol) was added in five portions over 1 hours. The resulting mixture was stirred for 1 hour at room temperature. At this point, 0.5N aqueous hydrochloric acid solution (1000 mL) was slowly added, and the mixture was extracted with 50% ethyl acetate in hexanes (2000 mL×3). The combined organic extracts were washed with 10% $NaHCO_3$ (2000 mL×3), dried over anhydrous magnesium sulfate, and filtered. The filtrate was evaporated under reduced pressure to obtain a residue of 6 as orange foam. Silica gel column chromatography (30% ethyl acetate in hexanes as eluant) provided 121.9 g of compound 6 as yellow oil.

(b). Preparation of 1α-acetoxy-3,5-cyclo-(20S)-(tert-Butylmethylsilyloxy)-10-oxo-19-nor vitamin D2 1-acetate, 6-methyl ether 1-acetate (7)

The compound 6 (121 g, 0.30 mol) was dissolved in dichloromethane (972 g), and imidazole (11.3 g, 0.16 mmol) and TBDMS-chloride (45.2 g, 0.30 mol) were added. The mixture was stirred at 20° C. for 90 minutes and then partitioned between EtOAc (1000 mL) and water (1000 mL). The organic layer was washed twice with water and brine, dried and concentrated to give a crude product (Compound 7, 155 g) as yellow foam that used without purification in the next step.

Compound 7 $^1$HNMR:

$^1$HNMR(200 MHz, $CDCl_3$): δ5.17(m,1H), 4.98(d,1H, J=9.4 Hz), 4.56(d,1H,J=9.4 Hz), 3.54(d,1H,J=3.2 Hz,), 3.27 (d,1H,J=7.2 Hz), 3.18(s,3H), 2.72~2.77(m,1H), 2.32~2.20 (m,1H), 2.11(s,3H), 1.95~1.98(m,1H), 1.14~1.95(m,15H), 0.98(d,3H,J=6.20Hz),0.84(s,9H), 0.51(s,3H), 0.14(s,6H).

(c). Preparation of 1α-acetoxy-3,5-cyclo-(20S)-(tert-Butylmethylsilyloxy)-10-hydroxy-19-nor vitamin D2 1-acetate, 6-methyl ether 1-acetate (9)

The compound 7 residue (155 g, 0.30 mol) was dissolved in methanol (292 g) and THF (645 g) and cerium (III) chloride hexahydrate (335 g, 0.89 mol). The mixture was agitated and cooled to below 10° C. followed by the addition of sodium borohydride (11.3 g, 0.30 mol). After reaction completion, the reaction mixture was quenched by the addition of saturated ammonia chloride solution (500 mL), the mixture was agitated for about 30 minutes and then concentrated under vacuum to give residue. To the residue was added 50% ethyl acetate in hexanes (100 mL×3) followed by phase separation. The organic extracts was washed with aqueous $NaHCO_3$ (250 mL), followed by phase separation. The organic layer was washed with water (250 mL×2), followed by concentrated to dryness under vacuum to give compound 9 crude as yellow foam. Silica gel column chromatography (10% ethyl acetate in hexanes as eluant) provided 130 g of compound 9 as yellow oil.

$^1$HNMR(200 MHz, $CDCl_3$): δ5.17(m,1H), 4.60~4.68(m, 2H), 4.08~4.11(m,1H), 3.58(d,1H,J=2.4 Hz,), 3.26(d,1H, J=7.5 Hz), 3.18(s,3H), 2.72~2.77(m,1H), 2.11(s,3H), 2.02~2.07(m,1H), 1.14~1.95(m,17H), 0.94(d,3H,J=6.80Hz), 0.85(s,9H), 0.52(s, 3H), 0.008(s,6H).

Example 4

Preparation of 1α-acetoxy-3,5-cyclo-(20S)-(tert-Butylmethylsilyloxy)-10-hydroxyl-19-nor vitamin D2 1-acetate, 6-methyl ether 1-acetate (9)

(a). Preparation of 1α-acetoxy-3,5-cyclo-10,20S-diol-19-nor vitamin D2 1-acetate, 6-methyl ether 1-acetate (8)

In 100 mL, three-neck, was charged the 10-oxo derivative compound (5) (R=Ac, 2.51 g, 4.04 mmol), methanol (6.66 mL) and THF (13.32 mL) and cerium (III) chloride hexahydrate (3.0 g, 8.08 mmol). The mixture was agitated and cooled to below 10° C. followed by the addition of sodium borohydride (3.0 eq, 0.15 g, 4.04 mol). After reaction completion, the reaction mixture was quenched by the addition of saturated ammonia chloride solution (10 mL), the mixture was agitated for about 30 minutes and then concentrated under vacuum to give residue. To the residue was added 50% ethyl acetate in hexanes (10 mL×3) followed by phase separation. The organic extracts was washed with aqueous $NaHCO_3$ (10 mL), followed by phase separation. The organic layer was washed with water (10 mL×2), followed by concentrated to dryness under vacuum to give compound 8 crude as yellow foam that used without purification in the next step.

(b). Preparation of 1α-acetoxy-3,5-cyclo-(20S)-(tert-Butylmethylsilyloxy)-10-hydroxy-19-nor vitamin D2 1-acetate, 6-methyl ether 1-acetate (9)

The compound 8 residue (0.69 g, 1.29 mmol) was dissolved in dichloromethane (4.2 mL), and imidazole (0.26 g, 3.88 mmol) and TBDMS-chloride (1.05 eq, 0.29 g, 1.92 mmol) were added. The mixture was stirred at 10° C. for 90 minutes and then partitioned between EtOAc (10 mL) and water (10 mL). The organic layer was washed twice with water and brine, dried and concentrated to give a crude product (Compound 8, 0.80 g) as yellow foam. Silica gel column chromatography (10% ethyl acetate in hexanes as eluant) provided 5.2 g (30% yield) of compound 9 as yellow oil.

Example 5

Preparation of 1α-acetoxy-3,5-cyclo-(20S)-(tert-Butylmethylsilyloxy)-19-nor vitamin D2 1-acetate, 6-methyl ether 1-acetate (12)

(a). Preparation of 1α-hydroxy-3,5-cyclo-(20S)-(tert-Butylmethylsilyloxy)-19-nor vitamin D2 1-ol, 6-methyl ether (11)

The 10-alcohol (compound 9, 130 g, 0.25 mol) was dissolved in Toluene (1118 g) and triethylamine (152 g, 1.5 mmol). The mixture was cooling to below 0° C., followed by added mesyl chloride solution (51.7 g, 0.45 mol). The mixture was stirred at 0° C. for 2 hour or until the reaction completed. The $LiAlH_4$ (56.9 g, 1.49 mol) was added, and followed by anhydrous THF (10.7 g) added at −10° C. The mixture kept at 0° C. for 2 h. Excess $LiAlH_4$ was decomposed with $H_2O$, followed by phase separation. The organic layer was washed by water and dried over $MgSO_4$, filtered and evaporated to give the crude 19-nor product (compound 11). The compound 11 crude is purified by fraction collection using the flash column chromatography to give compound 11 (71.5 g, 0.15 mol).

(b) Preparation of 1α-acetoxy-3,5-cyclo-(20S)-(tert-Butylmethylsilyloxy)-19-nor vitamin D2 1-acetate, 6-methyl ether 1-acetate (12)

Compound 11 (71.5 g, 0.15 mol) was dissolved in dry pyridine (350 g) and acetic anhydride (46 g, 0.45 mol). The reaction was added 4-Dimethylaminopyridine (DMAP, 3.78 g, 0.03 mol) and kept at room temperature for about 1 hour, then diluted with 10% $NaHCO_3$ solution (214 mL). This solution is extracted with ethyl acetate (500 mL×3) and the organic extracts were washed with $H_2O$ (500 mL×3), dried over $MgSO_4$, and the solvent was removed in vacuo to give crude compound 12 (95.1 g,) that was used without purification in the next step.

$^1HNMR(600$ $MHz,CDCl_3)$: δ4.86(d,1H,J=9.06 Hz), 4.70~4.75(m,1H), 3.83(d,1H,J=9.18 Hz,), 3.54(dd,1H, J=9.60 Hz), 3.21~3.25(m,1H), 3.18(s,3H), 2.49~2.52(m, 1H), 2.14~2.21(m,2H), 1.94(s,3H), 1.14~1.91(m,15H), 0.95 (d,3H,J=6.54 Hz), 0.84(s,9H), 0.45~0.56(m,4H), 0.32(tr,1H, J=6.9 Hz), 0.02(s,6H).

Example 6

Preparation of 1α-tert-Butylmethylsilyloxy-3,5-cyclo-(20S)-tosylate-19-nor vitamin D2 1-tert-Butylmethylsilyloxy, 6-methyl ether 1-tert-Butylmethylsilyloxy (16)

(a). Preparation of 1α-acetoxy-3,5-cyclo-(20S)-hydroxy-19-nor vitamin D2 1-acetate, 6-methyl ether 1-acetate (13)

The compound 12 (95.1 g, 0.18 mol) obtained by above was dissolved in THF (378 g), and imidazole (2.1 g, 0.03 mol), TBAF (tertabutylammonium fluoride, 10 g, 0.31 mol) were added. The reaction mixture was heated under reflux 1 hour or until TLC analysis (silica gel plates, 30% ethyl acetate in hexanes) indicated that no starting material remained. The reaction was cooled to room temperature, and was concentrated under reduced pressure. The crude residue was dissolved in ethyl acetate (193 g) and washed with $H_2O$ (250 g×2). The extracts was dried over dried over $MgSO_4$, and the solvent was removed in vacuo to give crude compound 13 (74.2 g, 0.18 mol) that was used without purification in the next step.

$^1HNMR(600$ MHz, $CDCl_3)$: δ4.85(d,1H,J=9.12 Hz), 4.70~4.72(m,1H), 3.82(d,1H,J=9.18 Hz), 3.56~3.59(m,1H), 3.29~3.32(m,1H), 3.16(s,3H), 2.48~2.52(m,1H), 2.13~2.19 (m,1H), 1.97(s,3H), 1.14~1.91(m,15H), 0.99(d,3H,J=6.60 Hz), 0.53~0.54(m,1H), 0.52(s, 3H), 0.30~0.32 (m,1H). (311R001).

(b). Preparation of 1α-acetoxy-3,5-cyclo-(20S)-tosylate-19-nor vitamin D2 1-acetate, 6-methyl ether 1-acetate (14)

The compound 13 crude (74.2 g, 0.18 mol) obtain by above was dissolved in dichloromethane (285 g), pyridine (207 g), DMAP (3.8 g, 0.03 mol) and p-toluene-sulfonyl chloride (46 g, 0.24 mol) were added under nitrogen.

The mixture is allowed to react for 2 hr at 30° C., and is then quench with 50 mL of 10% $NaHCO_{3(aq)}$. The aqueous phase is extracted with ethyl acetate (200 g×2) and the ether acetate extract is washed with 10% $NaHCO_3$ (200 mL×2), and $H_2O$ (300 g×2). The solvent is removed in vacuo and the crude residue (compound 14, 93.9 g, 0.17 mol, (20S)-tosylate-19-nor Cyclovitamin $D_2$).

$^1$HNMR(600 MHz, CDCl$_3$): δ 7.75(d, 2H, J=8.20 Hz), 7.31(d, 2H,J=8.10 Hz), 4.87(d,1H,J=9.06 Hz), 4.73~4.75(m, 1H), 4.07~4.10(m,1H), 3.92~3.95(m,2H), 3.83(d,1H, J=9.18 Hz), 3.77~3.79(m, 1H), 3.19(s,3H), 2.51~2.52(m,1H), 2.42 (s, 3H), 2.20~2.22(m,2H), 2.00(s, 3H), 1.14~1.93(m,15H), 0.97(d,3H,J=6.60 Hz), 0.55~0.56(m,1H), 0.49(s,3H), 0.32~0.35(m,1H). (311R002)

(c). Preparation of 1α-hydroxy-3,5-cyclo-(20S)-tosylate-19-nor vitamin D2 1-ol, 6-methyl ether 1-hydroxy (15)

The compound 14 (93.9 g, 0.17 mol) was dissolved in a methanol (318 g) and 20% NaOH (71.5 mL) was added. The mixture was stirred under nitrogen atmosphere for 2 hour. After reaction completion, the reaction mixture was concentrate to remove organic solvent. The residue was extract by ethyl acetate (202 g). The organic phase washed with brine, dried over MgSO$_4$, filtered and evaporated to give residue (compound 15, 81.8 g, 0.16 mol) that used without purification in the next step.

$^1$HNMR(600 MHz, CDCl$_3$): δ 7.76(d, 2H, J=8.16 Hz), 7.32(d, 2H,J=8.04 Hz), 4.80(d,1H,J=9.18 Hz), 4.07~4.11(m, 1H),4.01(br, 1H), 3.92~3.95(m,2H), 3.77~3.80(m,1H), 3.21 (s,3H), 2.52~2.53(m,1H), 2.42(s, 3H), 2.11~2.13(m,1H), 2.01(s, 3H), 1.14~1.98(m,23H), 0.97(d,3H,J=6.60 Hz), 0.64~0.66(m,1H), 0.49(s, 3H), 0.31~0.33(m,1H). (311R003).

(d). Preparation of 1α-tert-Butylmethylsilyloxy-3,5-cyclo-(20S)-tosylate-19-nor vitamin D2 1-tert-Butylmethylsilyloxy, 6-methyl ether 1-tert-Butylmethylsilyloxy (16)

The compound 15 (81.8 g, 0.16 mol) was dissolved in dichloromethane (570 g), and imidazole (31.5 g, 0.46 mol) and TBDMS-chloride (27.9 g, 0.19 mol) were added. The mixture was stirred at 20° C. for 90 minutes and then partitioned between EtOAc (202 g) and water (200 g). The organic layer was washed twice with water and brine, dried and concentrated to give a crude product (Compound 16). Silica gel column chromatography (10% ethyl acetate in hexanes as eluant) provided 66.7 g (0.11 mol) of compound 16 as yellow oil.

$^1$HNMR(600 MHz,CDCl$_3$): δ 7.76(d, 2H, J=8.22 Hz), 7.32 (m, 2H), 4.93 (d,1H,J=9.0 Hz), 3.94~3.95(m,1H),3.89~3.93 (m, 1H), 3.74~3.79(2H, m), 3.18(s,3H), 2.52~2.53(m,1H), 2.42(s, 3H), 1.05~1.98(m,26H), 0.96~0.99(m,1H), 0.88(s, 9H), 0.83(s,2H), 0.52(s,1H), 0.06(s,6H), 0.009 (d,J=2.76 Hz, 1H).

Example 7

Preparation of 1α-tert-Butylmethylsilyloxy-3,5-cyclo-(20S) -(diphenylphosphonium)-19-nor vitamin D2 1-tert-Butylmethylsilyloxy, 6-methyl ether 1-acetate (18)

(a). Preparation of 1α-tert-Butylmethylsilyloxy-3,5-cyclo-(20S)-iodomethyl-19-nor vitamin D2 1-tert-Butylmethylsilyloxy, 6-methyl ether 1-acetate (17)

The compound 16 (60 g, 97.2 mmol) was dissolved in acetone (324 g) and sodium iodine (32 g, 0.21 mol). The mixture was under reflux for 2.5 hour or until TLC analysis (silica gel plates, 20% ethyl acetate in hexanes) indicated that no starting material remained. The reaction mixture was cooled and the solvent was evaporated under reduced pressure to afford a residue. The residue was dissolved in ethyl acetate (200 g) and washed with H$_2$O (200 g×3). The extracts was dried over an). The extracts was dried over anhydrous magnesium sulfate and filtered. The filtrate was evaporated under reduced pressure to obtain Compound 17 as orange foam that was used without purification in the next step.

(b) Preparation of 1α-tert-Butylmethylsilyloxy-3,5-cyclo-(20S)-(diphenylphosphonium)-19-nor vitamin D2 1-tert-Butylmethylsilyloxy, 6-methyl ether 1-acetate (18)

In 2 L, three-neck, round-bottom flask equipped with a mechanical stirrer, thermocouple, nitrogen bubbler, and two pressure-equalizing addition funnels was charge diphenylphosphine (27 g, 0.14 mol) and dry THF (300 g). The stirrer was started, and the solution was cooled to −78° C. To one addition funnel was charged n-butyllithium (1.5M solution in hexanes, 136 mL), and this was slowly added to the cooled solution, producing a reddish-orange mixture that was stirred at −78° C. for 45 minutes. A solution of compound 17 was obtain above in dry THF (300 g) was transferred to the second addition funnel, and this solution was added to the reaction stirred for 45 minutes at −78° C. and then gradually warmed to ambient temperature where it was stirred for 3 hour. The reaction mixture was diluted with methyl tert-butyl ether (TBME, 444 g) and washed with saturated aqueous ammonium chloride solution (500 mL). The organic layer was gently washed with 10% hydrogen peroxide solution (10% H$_2$O$_2$, 120 mL). The organic layer was then washed with saturated aqueous sodium chloride solution (300 mL×2), dried over anhydrous magnesium sulfate, and clarified. The yellow filtrate was evaporated under reduced pressure to afford the crude product as yellow oil. Silica gel column chromatography (30% ethyl acetate in hexanes as eluant) provided compound 18 (42.8 g, 66.1 mmol) as yellow oil.

$^1$HNMR(600 MHz,CDCl$_3$): δ7.71~7.74(m, 4H), 7.41~7.49(m, 6H), 4.91(d,1H,J=9.18 Hz, 7-H), 3.88~3.93(m, 1H), 3.76(d,1H,J=9.18 Hz), 3.19(s,3H), 2.51~2.54(m,1H), 2.36~2.40(m,1H), 1.88~2.04(m,8H), 1.67(s,3H), 1.58~1.61 (m,4H), 1.2

Example 8

Preparation of 1α-acetoxy-3-(tert-Butyldimethylsilyloxy)-(20S)- (diphenylphosphonium)-19-nor vitamin D2 (19)

The compound 18 (37.6 g, 58.1 mmol) was dissolved in acetic acid (188 mL) and stirred at 55° C. for 1 hour. The mixture was cooled, ice water added extracted with ethyl acetate. The other phase was washed with cold 10% sodium bicarbonate solution, brine, dried over with MgSO$_4$, filtered and evaporated to give the crude compound 19 (39 g). The crude compound 19 was purified by column chromatography to give compound 19.

Example 9

Preparation of 1α,3-(ditert-Butyldimethylsilyloxy)-(20S)- (diphenylphosphonium)-19-nor vitamin D2 (21)

The compound 19 (39 g, 57.8 mmol) was dissolved in a methanol (300 g) and 20% NaOH (37.6 mL) was added. The mixture was stirred under nitrogen atmosphere for 2 hour. After reaction completion, the reaction mixture was concentrate to remove organic solvent. The residue was extract by ethyl acetate (202 g). The organic phase washed with brine, dried over MgSO$_4$, filtered and evaporated to give residue (compound 20, 43.4 g) that used without purification in the next step.

The compound 20 was dissolved in dichloromethane (300 g), and imidazole (11.8 g, 0.17 mol) and TBDMS-chloride (13 g, 86.2 mmol) were added. The mixture was stirred at 20° C. for 90 minutes and then partitioned between EtOAc (202 g) and water (200 g). The organic layer was washed twice with water and brine, dried and concentrated to give a crude product (Compound 21). Silica gel column chromatography (10% ethyl acetate in hexanes as eluant) provided 24.4 g, 32.6 mmol) of compound 21 as white powder.

$^1$HNMR (600 MHz, CDCl$_3$):

δ7.71~7.74(m, 4H), 7.43~7.48(m, 6H), 6.11(d,1H, J=11.16 Hz), 5.75(d,1H,J=11.1 Hz), 4.03(br, 2H), 2.74~2.77 (m,1H), 2.29~2.41 (m,3H), 1.87~2.08(m,5H), 1.73(s,3H), 1.16~1.65(m,6H), 1.06(d,3H, J=6.18 Hz), 1.11(s,3H), 0.86(s, 9H), 0.83 (m,9H), 0.44(s, 3H), 0.03(s,12H).

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The processes for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. A compound having formula I wherein X$_1$ is OH, O-acyl, O—C$_{1-8}$ alkylsilyl or O—C$_{1-8}$ alkyloxy-C$_{1-8}$ alkyl;

wherein X$_2$ is C$_{1-6}$ alkoxy; and wherein X$_3$ is chlorine, bromine, iodine, O-tosyl or O-mesyl.

2. The compound according to claims 1 wherein X$_2$ is methoxy.

3. The compound according to claim 1 wherein X$_1$ is hydroxyl, O-acyl or O- tert-butyldimethylsilyl.

4. The compound according to claims 1 wherein X$_3$ is iodine, O-tosyl or O-mesyl.

* * * * *